United States Patent
Matsui et al.

(10) Patent No.: US 9,709,425 B2
(45) Date of Patent: Jul. 18, 2017

(54) SENSOR WITH FOAMED RUBBER SEALING MEMBER MOUNTED TO CIRCUIT BOARD

(71) Applicant: NGK Spark Plug Co., LTD., Nagoya (JP)

(72) Inventors: Ryosuke Matsui, Koyosu (JP); Shingo Yoshida, Ichinomiya (JP); Shinichi Sawada, Konan (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 207 days.

(21) Appl. No.: 14/538,166

(22) Filed: Nov. 11, 2014

(65) Prior Publication Data

US 2015/0143901 A1 May 28, 2015

(30) Foreign Application Priority Data

Nov. 11, 2013 (JP) .................................. 2013-233415
Jun. 6, 2014 (JP) .................................. 2014-117785
Nov. 7, 2014 (JP) .................................. 2014-227153

(51) Int. Cl.
| | |
|---|---|
| *G01L 19/14* | (2006.01) |
| *G01D 11/24* | (2006.01) |
| *G01N 27/14* | (2006.01) |
| *G01N 33/00* | (2006.01) |

(52) U.S. Cl.
CPC ............ *G01D 11/24* (2013.01); *G01D 11/245* (2013.01); *G01L 19/147* (2013.01); *G01L 19/148* (2013.01); *G01N 27/14* (2013.01); *F01N 2560/024* (2013.01); *G01N 33/005* (2013.01)

(58) Field of Classification Search
CPC ...... G01D 11/24; G01D 11/245; G01D 11/26; G01L 19/147; G01L 19/148; G01N 2035/00306; F01N 2560/024
See application file for complete search history.

(56) References Cited

U.S. PATENT DOCUMENTS

| | | | |
|---|---|---|---|
| 6,745,633 B2 * | 6/2004 | Sasaki .................. | G01L 19/147 73/727 |
| 7,178,404 B2 * | 2/2007 | Lee ....................... | G01L 19/148 73/706 |
| 2012/0029400 A1 * | 2/2012 | Moretto ............. | A61H 23/0263 601/55 |

FOREIGN PATENT DOCUMENTS

JP 2008-267948 A 11/2008

* cited by examiner

*Primary Examiner* — Justin Olamit
(74) *Attorney, Agent, or Firm* — Leason Ellis LLP

(57) ABSTRACT

A sensor includes a sensor element; a circuit board having an element attachment surface on which the sensor element is mounted; a casing member for housing the circuit board, the casing member having a measurement chamber which faces the sensor element and communicates with the target atmosphere through a gas inlet; an annular elastic seal member which is interposed between the element attachment surface and the casing member in such a manner that the elastic seal member is in contact with the element attachment surface. The elastic seal member is made of foamed rubber and has an end surface flat portion which faces the casing member and another end surface flat portion which faces the element attachment. The elastic seal member is interposed between the element attachment surface and the casing member such that the elastic seal member is compressed between the flat portions of the end surfaces.

18 Claims, 3 Drawing Sheets

SENSOR WITH FOAMED RUBBER SEALING MEMBER MOUNTED TO CIRCUIT BOARD

This application claims the benefit of Japanese Patent Applications No. 2013-233415, filed Nov. 11, 2013, No. 2014-117785, filed Jun. 6, 2014 and No. 2014-227153, filed Nov. 7, 2014, all of which are incorporated by reference in their entities herein.

FIELD OF THE INVENTION

The present invention relates to a sensor for detecting a predetermined characteristic of an atmosphere to be detected, such as the gas concentration of a particular component of the atmosphere, the temperature of the atmosphere, or the humidity of the atmosphere.

BACKGROUND OF THE INVENTION

In recent years, in consideration of demand of society, such as environmental protection and nature conservation, researches have been actively conducted on a fuel cell, which is an efficient and clean energy source. In particular, a polymer electrolyte fuel cell (PEFC) and a hydrogen internal combustion engine, which operate at low temperature, have high output, and are high in density, are expected to be used in homes or be mounted on vehicles. However, since these energy sources use hydrogen as fuel, they require a sensor for detecting leakage of hydrogen.

Conventionally, a sensor for detecting the concentration of a flammable gas such as hydrogen has a known structure in which an element case holding a sensor element is disposed on a circuit board, which is housed in a housing case (casing member) formed of resin (see Japanese Patent Application Laid-Open (kokai) No. 2008-267948 (FIG. 2)). In this sensor, the housing case has an annular flow channel forming portion which projects downward from the center of a lower portion of the housing case and opens downward. The sensor element is disposed to face the interior of the flow channel forming portion, and a hermetic seal is established between the element case and the housing case by means of an O-ring formed of rubber. Thus, an internal space (measurement chamber) into which an atmosphere to be detected is introduced is formed between the element case and the flow channel forming portion, and the concentration of a flammable gas is detected by the sensor element.

Problem to be Solved by the Invention

Incidentally, the following problems arise in the case where a sensor element is mounted directly on a circuit board without use of an element case, this circuit board is housed in a casing member, and an O-ring is disposed between the circuit board and the casing member so as to form a measurement chamber.

First, when the O-ring is pressed against the circuit board under high pressure, a large stress (bending force) acts on the circuit board. As a result, wiring traces formed on the circuit board may be broken, and/or solder portions of electronic components, fittings, etc. may be broken.

Further, when the O-ring is pressed against the circuit board under high pressure, the casing member and the circuit board are firmly fixed to each other through the O-ring. Therefore, when an external impact acts on the casing member or the casing member expands thermally, the impact acting on the casing member or a force produced as a result of thermal expansion of the casing member act directly on the circuit board, and breakage of the above-described wiring traces or solder portions becomes more likely to occur.

The present invention has been accomplished in order solve the above-described problems, and its object is to provide a sensor in which a circuit board partially forms a measurement chamber and which prevents damage of the circuit board, which damage would otherwise occur when the circuit board is fixed to a casing member which houses the circuit board.

SUMMARY OF THE INVENTION

Means for Solving the Problem

In order to solve the above-described problem, the present invention provides a sensor comprising a sensor element which is exposed to an atmosphere to be detected (target atmosphere) and detects a predetermined characteristic of the atmosphere to be detected; a circuit board having an element attachment surface on which the sensor element is mounted; a casing member for housing the circuit board, the casing member having a measurement chamber which the sensor element faces and which communicates with the atmosphere to be detected through a gas inlet formed in the casing member; and an annular elastic seal member which is interposed between the element attachment surface and the casing member in such a manner that the elastic seal member is in contact with the element attachment surface. In the sensor, the elastic seal member is formed of foamed rubber; at least a portion of an end surface of the elastic seal member which faces the casing member and at least a portion of an end surface of the elastic seal member which faces the element attachment surface are rendered flat; and the elastic seal member is interposed between the element attachment surface and the casing member in a state in which the elastic seal member is compressed between the flat portions of the end surfaces.

According to this sensor, the elastic seal member is formed of soft foamed rubber and at least a portion of its end surface facing the element attachment surface is flat. Therefore, the elastic seal member is in surface contact with the element attachment surface. Also, since the elastic seal member is formed of soft foamed rubber, a satisfactory seal performance is attained even when the elastic seal member is pressed against the circuit board under a lower pressure as compared with the case where an O-ring is used, whereby the stress (bending force) acting on the circuit board is decreased. As a result, breakage of wiring traces formed on the circuit board and breakage of solder portions of electronic components, fittings, etc. soldered to the circuit board are restrained.

Further, since a satisfactory seal performance is attained even when the elastic seal member is not pressed against the circuit board under high pressure, the casing member and the circuit board are not firmly fixed to each other via the elastic seal member. As a result, even when an external impact acts on the casing member or the casing member expands thermally, the resultant stress is absorbed by, for example, shift of the elastic seal member, and the impact acting on the casing member and other stresses become less likely to act directly on the circuit board. Therefore, breakage of the above-described wiring traces and solder portions is restrained further.

Notably, although it is sufficient that the elastic seal member is interposed between the element attachment surface and the casing member, it is more preferred that the flat portions of the elastic seal member come into contact with the element attachment surface and the casing member in such a manner that a high degree of airtightness is maintained.

The sensor may be configured in such a manner that a wiring trace is formed on the element attachment surface of the circuit board, and at least a portion of the corresponding flat portion of the elastic seal member is in tight contact with the surface of the wiring trace.

According to this sensor, even in the case where irregularities stemming from wiring traces formed on the element mounting surface are present, the elastic seal member can be brought into tight contact with the element attachment surface. Therefore, it becomes unnecessary to change the circuit design for avoiding formation of wiring traces in a region where the element attachment surface and the elastic seal member come in tight contact with each other.

Notably, "tight contact" refers to a state in which the pressing force of the elastic seal member fully acts on the element attachment surface.

The sensor may be configured in such a manner that the end surface of the elastic seal member which faces the casing member is bonded to the casing member; and an inner surface of the elastic seal member forms at least a portion of an inner wall of the measurement chamber.

According to this sensor, unlike the case where an O-ring is disposed, a holding groove for holding the O-ring does not need to be formed on the casing member, and manufacture of the casing member becomes easy. Also, since the inner surface of the elastic seal member forms a portion of the inner wall of the measurement chamber, the shape of the casing member becomes simple, and the amount of material of the casing member used for the measurement chamber can be reduced.

The sensor may be configured in such a manner that a cross section of the elastic seal member taken orthogonal to the flat portions has a rectangular shape in a no-load condition.

According to this sensor, the percentage of the flat portions of the end surfaces of the elastic seal member becomes high, and the elastic seal member can be brought into tight contact with the casing member and the element attachment surface, which are counterpart members, more reliably.

The foamed rubber may have a plurality of closed-cells.

According to this sensor, the gas which is the atmosphere to be detected cannot escape to the outside through the cells of the foamed rubber, whereby the sealing performance is enhanced. Therefore, use of the foamed rubber having a plurality of closed-cells is preferred.

Effect of the Invention

According to the present invention, there can obtained a sensor in which a circuit board partially forms a measurement chamber and which prevents damage of the circuit board, which damage would otherwise occur when the circuit board is fixed to a casing member which houses the circuit board.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Modes for Carrying Out the Invention

Embodiments of the present invention will now be described.

Figure 1:
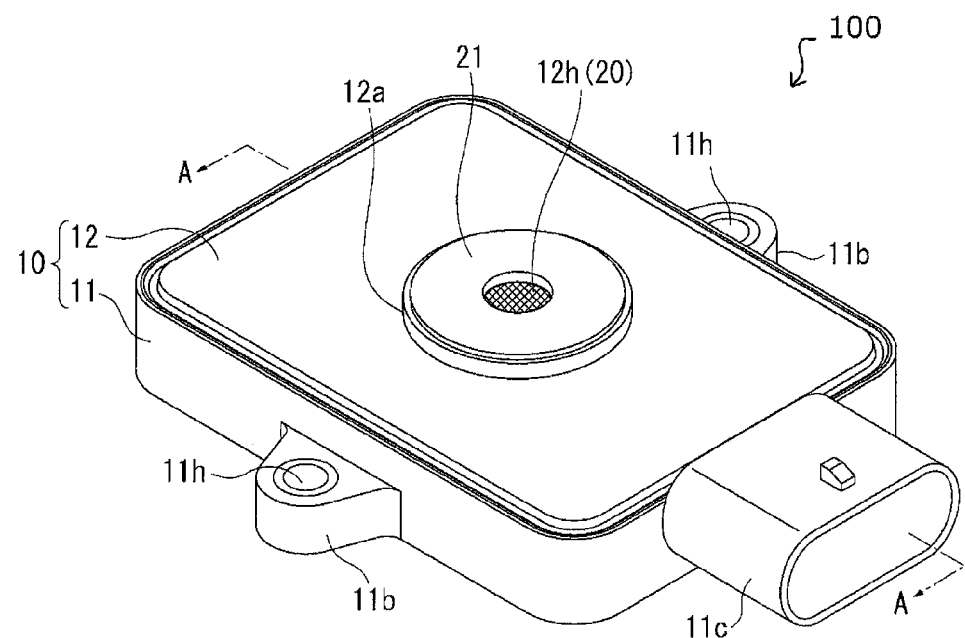
FIG. 1 is a perspective view of a sensor according to an embodiment of the present invention.
Figure 2:
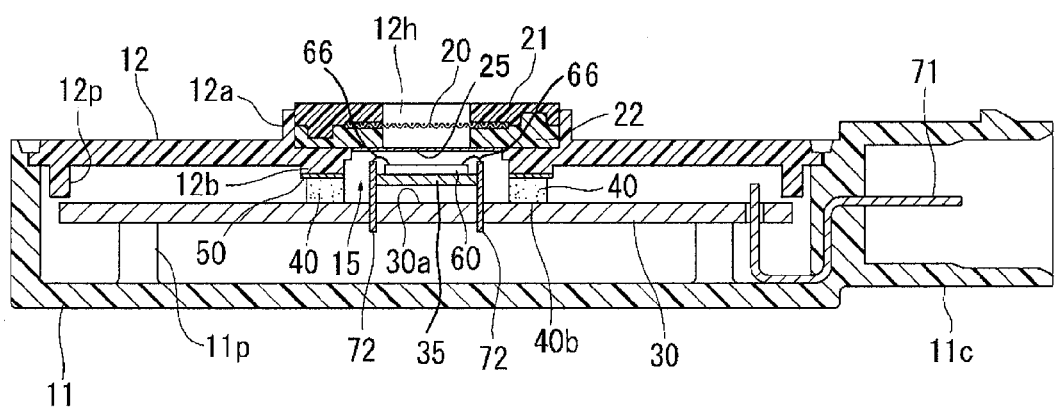
FIG. 2 is a sectional view taken along line A-A of FIG. 1.
Figure 3:
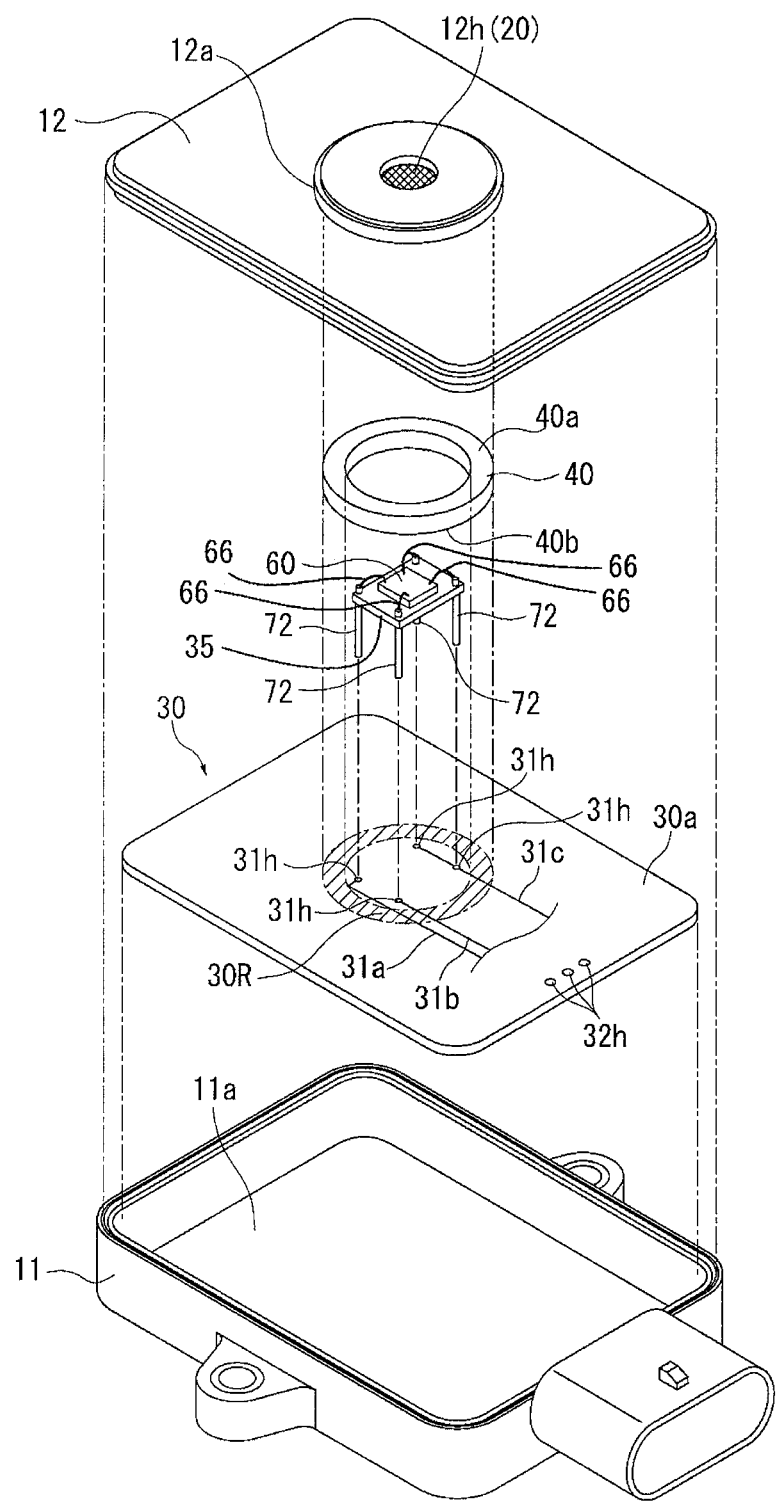
FIG. 3 is an exploded perspective view of the sensor.

FIG. 1 is a perspective view of a sensor 100 according to an embodiment of the present invention. FIG. 2 is a sectional view taken along line A-A of FIG. 1. FIG. 3 is an exploded perspective view of the sensor 100. Notably, in the following description, "upper surface" and "lower surface" are defined with respect to the vertical direction in FIGS. 1 through 3.

As shown in FIG. 1, the sensor 100 includes a casing member 10 formed of plastic or the like and having a generally rectangular box-like shape. The casing member 10 is composed of a casing main body portion 11 and a generally flat top plate 12 which closes a top opening 11a (see FIG. 3) of the casing main body portion 11.

A flange portion 11b extends outward from a central portion of each of two long sides of the casing main body portion 11, and a bolt hole 11h is formed at the center of each flange portion 11b. Bolts (not shown) passing through the bolt holes 11h are screwed into an object to which the sensor 100 is to be attached (for example, a predetermined portion of a vehicle), whereby the sensor 100 is attached to the object. Also, a tubular connector portion 11c for exchanging signals with an external device extends outward from one short side of the casing main body portion 11.

Meanwhile, an annular member 12a projects upward from a central portion of the top plate 12. A gas inlet 12h is open inside the annular member 12a, and the atmosphere to be detected flows between the inside and outside of the casing member 10 through the gas inlet 12h. As shown in FIG. 2, the top plate 12 including the annular member 12a is formed around upper and lower annular mesh holders 21 and 22 by means of insert molding, and inner openings of the upper and lower mesh holders 21 and 22 serve as the gas inlet 12h. Further, a metal mesh 20 is held between the upper and lower mesh holders 21 and 22, and the metal mesh 20 covers the gas inlet 12h. Also, a water repellent filter 25 is disposed on the lower surface of the lower mesh holder 22 (located on the lower side of the metal mesh 20) in such a manner that the water repellent filter 25 covers the gas inlet 12h to thereby prevent entry of water into the sensor 100 through the gas inlet 12h. The water repellent filter 25 may be disposed on the upper side of the metal mesh 20 (for example, on the upper surface of the upper mesh holder 21) in such a manner as to cover the gas inlet 12h.

Notably, the sensor 100 is a hydrogen gas sensor for measuring the hydrogen concentration of the atmosphere to be detected. Also, the metal mesh 20 serves a flame arrester which has an explosion prevention function. Therefore, even when the temperature of a sensor element 60 (see FIGS. 2 and 3) disposed within the casing member 10 becomes higher than the ignition temperature of hydrogen gas and the hydrogen gas ignites inside the casing member 10, a produced flame is prevented from escaping to the outside of the casing member 10. However, in the case where the sensor 100 is a temperature sensor or the like, the explosion prevention function is unnecessary, and the metal mesh 20 may be omitted.

As shown in FIGS. 2 and 3, the sensor 100 includes the sensor element 60, a circuit board 30, and the above-described casing member 10 for housing the sensor element 60 and the circuit board 30. The sensor element 60 is disposed (mounted) on the upper surface (element attachment surface) 30a of the circuit board 30 via a rectangular pedestal 35 to be described later. Meanwhile, inside the casing main body portion 11, a plurality of legs 11p project upward from the bottom of the casing main body portion 11, and come into contact with the lower surface (surface opposite the element attachment surface 30a) of the circuit board 30, to thereby position the circuit board 30 within the casing main body portion 11. When the circuit board 30 is disposed in the casing main body portion 11 and the top plate 12 is fitted to the inner edge of the top opening 11a of the casing main body portion 11, an elastic seal member 40 bonded to the lower surface of the top plate 12 as will be described later presses the element attachment surface 30a of the circuit board 30, to thereby fix the circuit board 30. At that time, the circuit board 30 is disposed in such a manner that the sensor element 60 faces toward the gas inlet 12h.

Notably, the top plate 12 is fixed to the casing main body portion 11 by means of adhesive, welding, or the like. Also, protrusions 12p function as guides when the top plate 12 is disposed in the top opening 11a, and do not come into contact with the element attachment surface 30a of the circuit board 30.

A microcomputer and various types of electronic components (not shown) for controlling the sensor element 60 are mounted on the circuit board 30 by means of soldering or the like. Also, a plurality of (three in this example) wiring traces 31a to 31c for electrical connection with the sensor element 60 are formed on the circuit board 30, and a through-hole 31h is formed at one end of each wiring trace 31a to 31c. The four through-holes 31h are respectively provided at the positions of four corners of a rectangle. A pin-shaped connection terminal 72 inserted into each through-hole 31h projects upward from the through-hole 31h beyond the element attachment surface 30a. The pedestal 35 is disposed above the element attachment surface 30a of the circuit board 30. Projecting portions of the connection terminals 72 penetrate through the four corners of the pedestal 35, and support the pedestal 35 in a state in which the pedestal 35 is separated from the circuit board 30. The sensor element 60 is disposed at a central portion of the upper surface (the surface facing toward the gas inlet 12h) of the pedestal 35. The upper ends of the connection terminals 72 project upward from the upper surface of the pedestal 35 and surround the sensor element 60. Meanwhile, a plurality of (four in this example) electrodes 63a, 63b, 65a, and 65b are formed on the surface of the sensor element 60 (see FIG. 4), and the electrodes 63a, 63b, 65a, and 65b are connected, through bonding wires 66, to the corresponding connection terminals 72 projecting from the upper surface of the pedestal 35. The connection terminals 72 are inserted into the corresponding through-holes 31h and are soldered, whereby the sensor element 60 is mounted on the circuit board 30. Notably, two through-holes 31h are formed in the wiring trace 31c which is common ground wiring, and the electrodes 63b and 65b which are ground electrodes are inserted into the two through-holes 31h via the corresponding connection terminals 72.

Further, a plurality of (three in this example) through-holes 32h electrically connected to the wiring traces 31a to 31c are formed along one short side of the circuit board 30. Inner ends of three male connector pins 71 housed within the connector portion 11c are inserted into the through-hole 32h and are soldered.

Meanwhile, an annular gas guide wall 12b which surrounds the outer circumference of the gas inlet 12h projects downward from the lower surface of the top plate 12. The annular elastic seal member 40 formed of foamed rubber is interposed between the gas guide wall 12b and the element attachment surface 30a of the circuit board 30. The upper surface (end surface facing the casing member) 40a of the elastic seal member 40 and the lower surface (end surface facing the element attachment surface) 40b thereof are flat. The upper surface 40a is in tight contact with the gas guide wall 12b via a bonding layer 50, and the lower surface 40b is in tight contact with the element attachment surface 30a. Notably, the inner diameter of the elastic seal member 40 is the same as the inner diameter of the gas guide wall 12b, and the elastic seal member 40 is disposed to overlap with the gas guide wall 12b. Also, the elastic seal member 40 has a rectangular cross section.

The inner space of the casing member 10 surrounded by the element attachment surface 30a, the gas inlet 12h, and the inner surface of the elastic seal member 40 forms a measurement chamber 15 in which the sensor element 60 is present and which communicates with the atmosphere to be detected. The concentration of hydrogen gas contained in the atmosphere to be detected within the measurement chamber 15 is detected by the sensor element 60.

As shown in FIG. 3, the lower surface 40b of the elastic seal member 40 is in tight contact with an annular region 30R of the element attachment surface 30a, and the annular region 30R extends across the wiring traces 31a to 31c. Since the elastic seal member 40 is formed of soft foamed rubber and at least a portion of the lower surface 40b is flat, the elastic seal member 40 is in surface contact with the annular region 30R. As a result, even in the case where irregularities stemming from the wiring traces 31a to 31c are present in a region (the annular region 30R) where the elastic seal member 40 is in tight contact with the element attachment surface 30a, the lower surface 40b can be brought into tight contact with the element attachment surface 30a, whereby the seal becomes reliable.

Also, since the elastic seal member 40 is formed of soft foamed rubber, a satisfactory seal performance is attained even when the elastic seal member 40 is pressed against the circuit board 30 under a lower pressure as compared with the case where an O-ring is used, whereby the stress (bending force) acting on the circuit board 30 is decreased. As a result, breakage of the wiring traces formed on the circuit board 30 and breakage of solder portions of electronic components, fittings (the male connector pins 71 and the connection terminals 72), etc. soldered to the circuit board 30 are restrained.

Further, since a satisfactory seal performance is attained even when the elastic seal member 40 is not pressed against the circuit board 30 under high pressure, the casing member 10 (the top plate 12) and the circuit board 30 are not firmly fixed to each other via the elastic seal member 40. As a result, even when an external impact acts on the casing member 10 (the top plate 12) or the casing member 10 expands thermally, the resultant stress is absorbed by, for example, shift of the elastic seal member 40, and the impact acting on the casing member 10 and other stresses become less likely to act directly on the circuit board 30. Therefore, the above-described breakage of the wiring traces and the solder portions is restrained further.

Also, in the case where an O-ring is interposed between the circuit board 30 and the casing member 10 (the top plate 12), the O-ring must be pressed against the circuit board 30 under high pressure in order to compress the O-ring. Therefore, structural components such as wall-shaped projections must be provided on the inner surface of the casing member 10. The wall-shaped projections are used to fix the O-ring from the radially inner side and radially outer side thereof. In contrast, according to the present embodiment, unnecessary structural components such as wall-shaped projections can be omitted. Therefore, the height of the sensor 100 can be reduced.

Notably, examples of the foamed rubber used to form the elastic seal member 40 include ethylene-propylene rubber (EPDM) and urethane rubber. Also, when the elastic seal member 40 is excessively compressed under high pressure, its flexibility is impaired. Accordingly, the elastic seal member 40 must be pressed (compressed) at a compressibility lower than the porosity (air content) of the foamed rubber used to form the elastic seal member 40; i.e., in a state in which all the cells of the foamed rubber are not crushed completely.

Also, if the cells of the foamed rubber used to form the elastic seal member 40 are closed-cells (the cells are present independently without being connected with one another), the gas which is the atmosphere to be detected cannot escape to the outside through the cells of the foamed rubber, whereby the sealing performance is enhanced. Therefore, use of foamed rubber having closed-cells is preferred.

Also, in the present embodiment, the elastic seal member 40 is bonded to the casing member (the gas guide wall 12b of the top plate 12), and the inner and outer surfaces of the elastic seal member 40 are exposed. In the case where the elastic seal member 40 is bonded to the casing member as described above, unlike the case where an O-ring is disposed, a holding groove for holding the O-ring does not need to be formed on the casing member (the top plate 12), and manufacture of the casing member becomes easy. Also, since the inner surface of the elastic seal member 40 forms a portion of the inner wall of the measurement chamber 15, the shape of the casing member becomes simple, and the amount of material of the casing member used for the measurement chamber 15 can be reduced.

Also, in the case where the elastic seal member 40 has a rectangular cross section in a no-load condition, the percentage of flat portions of the upper surface 40a and the lower surface 40b of the elastic seal member 40 becomes high, and the elastic seal member 40 can be brought into tight contact with the casing member 10 and the element attachment surface 30a, which are counterpart members, more reliably. Therefore, it is preferred that the elastic seal member 40 have a rectangular cross section in a no-load condition.

Figure 4:
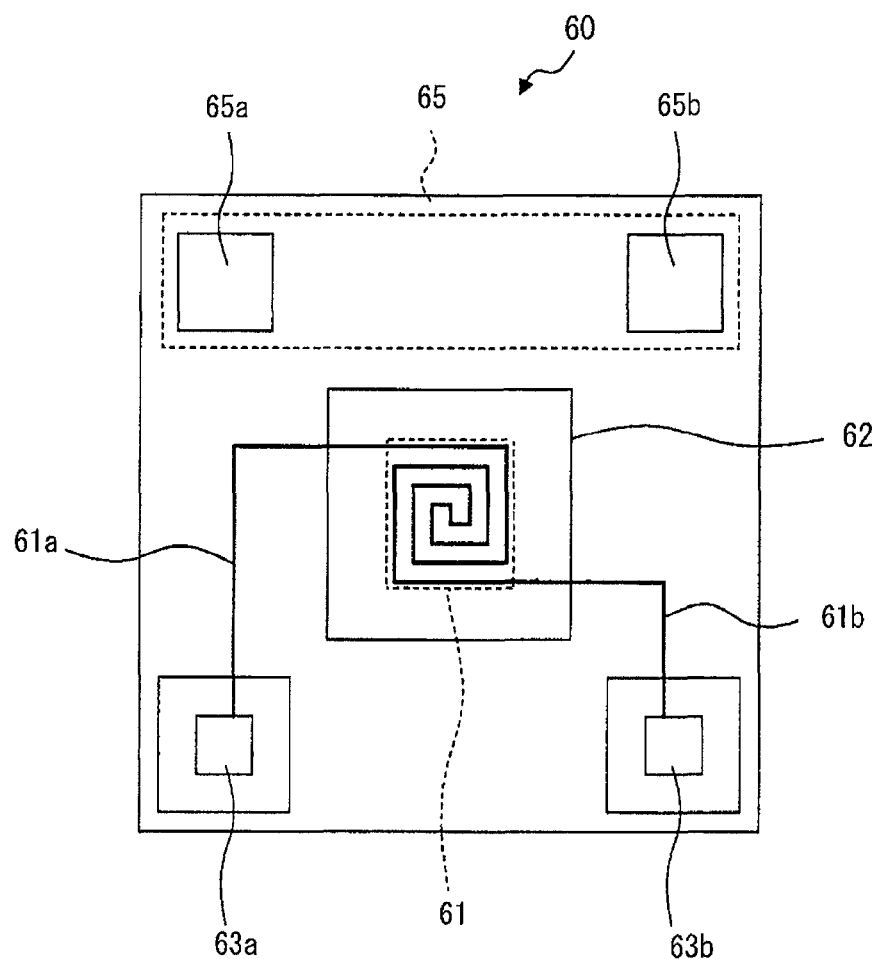
FIG. 4 is a plan view of a sensor element.

Next, the structure of the sensor element 60 will be described with reference to FIG. 4.

The sensor element 60 has the shape of a flat plate (a rectangular shape in a planar view), and the electrodes 63a, 63b, 65a, and 65b are formed at the four corners of the front surface thereof, and a recess 62 having a rectangular shape in a planar view is formed on the other surface (back surface) at a position near the center thereof such that the recess 62 is concave toward the front surface. The sensor element 60 is fabricated by forming an insulating layer on a silicon semiconductor substrate. In a region corresponding to the recess 62, a heat generation resistor 61 formed into a spiral pattern is embedded in the insulating layer (not shown).

The heat generation resistor 61 is a resistor whose resistance changes with the temperature of the resistor which changes with the temperature of the atmosphere to be detected (gas) (specifically, heat conduction to a flammable gas), and is formed of, for example, platinum (Pt). In the case where hydrogen gas is detected as a flammable gas, the amount of heat removed from the heat generation resistor 61 due to heat conduction to the hydrogen gas corresponds to the hydrogen gas concentration. Therefore, the hydrogen gas concentration can be detected on the basis of a change in the resistance of the heat generation resistor 61.

The left end of the heat generation resistor 61 is connected to the electrode 63a through a wiring trace 61a. The right end of the heat generation resistor 61 is connected to the electrode (ground electrode) 63b through a wiring trace 61b.

A temperature measurement resistor 65 for detecting the temperature of the atmosphere to be detected (gas) present within the measurement chamber 15 is embedded in the insulating layer (not shown) along one of the upper sides of the sensor element 60. The temperature measurement resistor 65 is formed of an electrically conductive material (for example, platinum (Pt)) whose resistance changes in proportion to the temperature (in the present embodiment, the resistance increases as the temperature increases).

The temperature measurement resistor 65 is connected to the electrode 65a and the electrode (ground electrode) 65b through a wiring film (not shown).

Needless to say, the present invention is not limited to the above-described embodiment, and encompasses various modifications and equivalents which fall within the scope of the present invention.

For example, in the above-described embodiment, the sensor 100 is a hydrogen gas sensor which is one type of gas sensor. However, the sensor 100 may be a flammable gas sensor in which, for example, an oxide semiconductor, a heat generation resistor, or a heat conduction element is used. Also, the sensor 100 is not limited to a gas sensor, and may be other types of sensors such as a temperature sensor and a humidity sensor.

Also, the shape of the elastic seal member 40 is not limited to that employed in the above-described embodiment. In the above-described embodiment, the elastic seal member 40 has an annular shape; i.e., the shape of a circular ring. However, the shape of the elastic seal member 40 is not limited thereto and may have the shape of a polygonal ring such as a rectangular ring.

Figure 5:
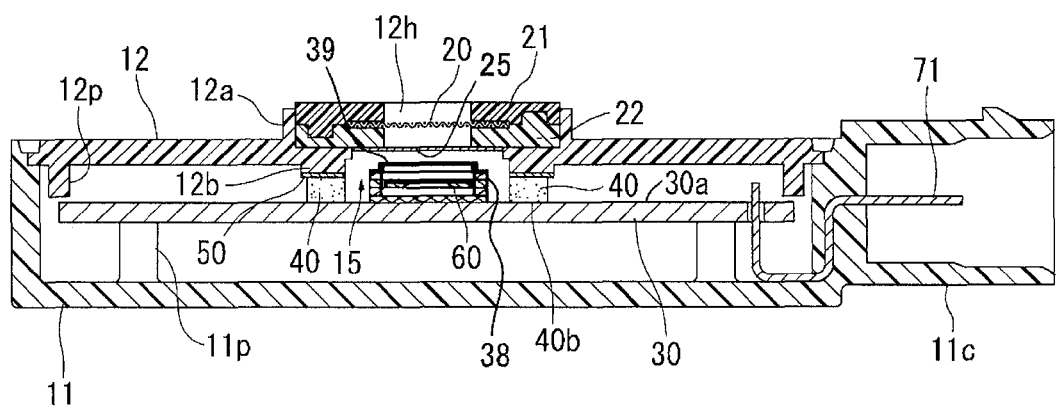
FIG. 5 is a sectional view of a sensor according to an embodiment in which a sensor element is surface mounted.

Moreover, the method of mounting the element 60 onto the circuit board 30 is not limited to the method employed in the above-described embodiment, and the element 60 may be mounted onto the circuit board 30 by means of surface mounting as shown in FIG. 5. Specifically, an element pedestal 38 for mounting the sensor element 60 is disposed on the upper surface (element attachment surface) 30a of the circuit board 30. The element pedestal 38 is formed into a generally rectangular parallelepiped by laminating a plurality of (four in FIG. 5) ceramic insulating layers each having insulating properties, and a recess for accommodating the sensor element 60 is formed. The sensor element 60 is fixed to the recess of the element pedestal 38 by means of an adhesive such as epoxy resin. Further, the electrodes 63a, 63b, 65a, and 65b on the surface of the sensor element 60 (see FIG. 4) are electrically connected to electrode pads provided on the element pedestal 38 through bonding wires or the like. The electrode pads of the element pedestal 38 are extended to the back surface of the element pedestal 38 through unillustrated internal wiring traces and are electrically connected to the wiring traces of the circuit board 30. In this manner, the sensor element 60 is surface mounted.

Further, a protection cap 39 is attached to the upper surface of the element pedestal 38 so as to cover the sensor element 60. Notably, the sensor element 60 faces the gas inlet 12h.

Also, in the above-described embodiment, the internal space surrounded by the element attachment surface 30a, the gas inlet 12h, and the inner surface of the elastic seal member 40 forms the measurement chamber 15. However, it is sufficient that the elastic seal member 40 serves as a seal between the element attachment surface 30a and the casing member 10, and the elastic seal member 40 is not required to form a portion of the measurement chamber 15.

DESCRIPTION OF REFERENCE NUMERALS

10: casing member
12h: gas inlet
15: measurement chamber
30: circuit board
30a: element attachment surface
31a-31c: wiring trace
40: elastic seal member
40a: end surface of the elastic seal member which faces the casing member
40b: end surface of the elastic seal member which faces the element attachment surface
60: sensor element
100: sensor

The invention claimed is:

1. A sensor comprising:
a sensor element which is exposed to a target atmosphere and detects a predetermined characteristic of the target atmosphere;
a circuit board having an element attachment surface on which the sensor element is mounted, a wiring trace being formed on the element attachment surface;
a casing member that houses the circuit board therein, the casing member having a measurement chamber which faces the sensor element and communicates with the target atmosphere through a gas inlet formed in the casing member; and
an annular elastic seal member which is interposed between the element attachment surface and the casing member in such a manner that the elastic seal member is in contact with the element attachment surface, wherein
the elastic seal member is made of foamed rubber;
the elastic seal member has an end surface portion which faces the casing member and another end surface portion which faces the element attachment surface, the end surface portion having at least a flat portion, and the other end surface portion having at least another flat portion; and
the elastic seal member is interposed between the element attachment surface and the casing member in a state in which the elastic seal member is compressed at the flat portion and the other flat portion.

2. The sensor according to claim 1, wherein at least a portion of the other flat portion is in tight contact with a surface of the wiring trace.

3. The sensor according to claim 1, wherein the end surface portion of the elastic seal member which faces the casing member is bonded to the casing member; and
an inner surface of the elastic seal member forms at least a portion of an inner wall of the measurement chamber.

4. The sensor according to claim 1, wherein a cross section of the elastic seal member taken orthogonal to the flat portion has a rectangular shape in a no-load condition.

5. The sensor according to claim 1, wherein the foamed rubber has a plurality of closed-cells.

6. The sensor according to claim 2, wherein the end surface portion of the elastic seal member which faces the casing member is bonded to the casing member; and
an inner surface of the elastic seal member forms at least a portion of an inner wall of the measurement chamber.

7. The sensor according to claim 2, wherein a cross section of the elastic seal member taken orthogonal to the flat portion has a rectangular shape in a no-load condition.

8. The sensor according to claim 3, wherein a cross section of the elastic seal member taken orthogonal to the flat portion has a rectangular shape in a no-load condition.

9. The sensor according to claim 2, wherein the foamed rubber has a plurality of closed-cells.

10. The sensor according to claim 3, wherein the foamed rubber has a plurality of closed-cells.

11. The sensor according to claim 4, wherein the foamed rubber has a plurality of closed-cells.

12. The sensor according to claim 6, wherein a cross section of the elastic seal member taken orthogonal to the flat portion has a rectangular shape in a no-load condition.

13. The sensor according to claim 6, wherein the foamed rubber has a plurality of closed-cells.

14. The sensor according to claim 7, wherein the foamed rubber has a plurality of closed-cells.

15. The sensor according to claim 12, wherein the foamed rubber has a plurality of closed-cells.

16. The sensor according to claim 1, wherein
the casing member comprises a top plate and a main body portion, said top plate being fitted to an inner edge of an opening portion of the main body portion, and
the elastic seal member is compressed between the top plate and the element attachment surface.

17. The sensor according to claim 1, wherein an inner surface of the elastic seal member is exposed to the target atmosphere in the measurement chamber.

18. The sensor according to claim 1, wherein at least a portion of the element attachment surface is exposed to the target atmosphere in the measurement chamber.

* * * * *